United States Patent [19]

Heumann

[11] Patent Number: 4,730,351

[45] Date of Patent: Mar. 8, 1988

[54] X-RAY DIAGNOSTICS INSTALLATION

[75] Inventor: Reiner Heumann, Erlangen, Fed. Rep. of Germany

[73] Assignee: Siemens Aktiengesellschaft, Berlin and Munich, Fed. Rep. of Germany

[21] Appl. No.: 865,628

[22] Filed: May 22, 1986

[30] Foreign Application Priority Data

Jun. 11, 1985 [DE] Fed. Rep. of Germany ....... 3520926

[51] Int. Cl.$^4$ ............................................. H05G 1/64
[52] U.S. Cl. ...................................... 378/99; 378/20; 378/205; 378/209; 378/163; 358/111
[58] Field of Search .......................... 378/20, 68–69, 378/95, 98–99, 162, 163, 205, 208–209; 128/653; 324/309, 318, 322; 358/125, 126

[56] References Cited

U.S. PATENT DOCUMENTS

| | | | |
|---|---|---|---|
| 2,823,316 | 2/1958 | Reynolds | 378/205 |
| 4,174,481 | 11/1979 | Liebetruth | 378/20 |
| 4,543,605 | 9/1985 | Verhoeven | 358/111 |
| 4,550,419 | 10/1985 | Aichinger et al. | 358/111 |
| 4,633,494 | 12/1986 | Klausz | 378/99 |

FOREIGN PATENT DOCUMENTS 2655661 6/1978 Fed. Rep. of Germany .
3147128 6/1983 Fed. Rep. of Germany .
3330552 3/1985 Fed. Rep. of Germany .

Primary Examiner—Craig E. Church
Assistant Examiner—John C. Freeman
Attorney, Agent, or Firm—Hill, Van Santen, Steadman & Simpson

[57] ABSTRACT

An X-ray diagnostics installation has a mechanism for positioning an examination subject within an X-ray beam and an X-ray image intensifier video chain with an image memory for displaying the radiated regions of the examination subject. A marker indicating the current position of the positioning mechanism is superimposed on the screen image of a visual display unit, thereby permitting adjustment of the position of the examination subject to a desired location without subjecting the patient to unwanted X-ray doses.

3 Claims, 1 Drawing Figure

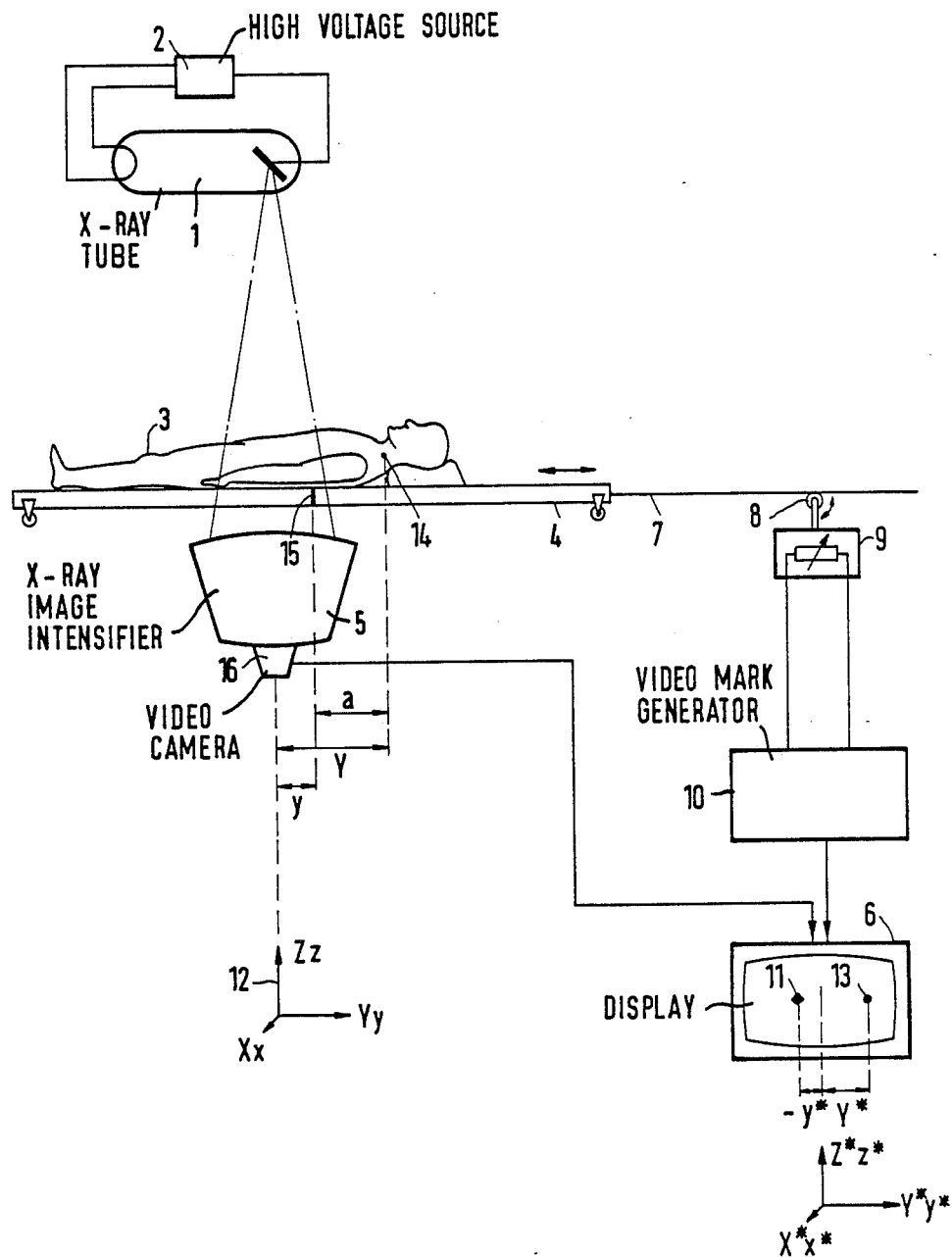

X-RAY DIAGNOSTICS INSTALLATION

BACKGROUND OF THE INVENTION

1. Field of the Invention

The present invention relates to X-ray diagnostics installations, and in particular to such installations having an adjustable bed on which the examination subject is disposed and having an image intensifier video chain with image storage capability.

2. Description of the Prior Art

An X-ray diagnostics installation as described in German OS No. 31 47 128 wherein positioning of the examination subject to a desired position can be undertaken during radiation of the patient with X-rays (transillumination check). The screen of the visual display unit shows the transilluminated regions of the patient, and thereby enables constant checking of the positioning operation. In order to maintain the radiation dose to which the examination subject is exposed as low as possible, the transillumination check can be undertaken with an X-ray dose rate which, though not adequate for a diagnosis, is sufficient for adjustment of the position of the examination subject. Despite these measures, the examination subject is still exposed to a constant radiation dose during the transillumination check.

Constant irradiation of the examination subject during positioning could be avoided by employing a visual display means with an image storage, however, this procedure frequently requires making several exposures (stored shots) until the desired position of the examination subject is reached. This method therefore also requires exposing the patient to a radiation dose which is relatively high.

SUMMARY OF THE INVENTION

It is an object of the present invention to provide an X-ray diagnostics installation with image storage and with a movable patient support system such that sufficiently precise position of the examination subject can be undertaken by means of only one stored shot.

The above object is achieved in accordance with the principles of the present invention by employing a measured value sensor for monitoring movement of the patient support bed. The measured value sensor generates an electrical signal corresponding to the position of the bed, and the signal is supplied to a video mark generator which generates a mark on the picture on the visual display unit which corresponds to the current position of the patient bed.

After exposure of the stored shot, the X-ray installation permits adjustment of the desired position without further radiation load on the examination subject.

DESCRIPTION OF THE DRAWINGS

The single FIGURE is a schematic block diagram of an X-ray diagnostic installation constructed in accordance with the principles of the present invention.

DESCRIPTION OF THE PREFERRED EMBODIMENTS

As shown in the FIGURE, an X-ray tube 1 is supplied with a high voltage generator 2. The x-rays generated thereby penetrate an examination subject 3 disposed on a movable bed 4. The bed 4 is transmissive for X-radiation and is movable in the y-direction, corresponding to the coordinate system 12. The image of the radiated regions of the patient 3 arising on the screen surface of an image intensifier 5 is converted into electrical signals in a video camera 16. The electrical signals are forwarded for visual display to a signal display unit 6. An image of the irradiated regions of the patient 3 can thus be seen on the screen of the visual display unit 6.

A video mark generator 10 generates a characteristic mark 11 on the screen of the visual display unit 6. The position of the characteristic mark 11 relative to the y-direction is defined by the value of resistance of a variable resistor 9. The value of the resistor 9 is directly proportional to the position of the bed 4 by virtue of a roller 8 and a drive rod 7 secured to the bed 4 which change the value of the variable resistor 9 as the bed 4 is moved. The y-position of the mark 11 on the visual display unit 6 is thus defined by the y-position of the bed 4.

The following discussion demonstrates that an adequately precise positioning of the patient in one dimension can be achieved with only one stored shot by the apparatus shown in the drawing.

The following variables are used in the discussion below:

Y Position of the location of the patient to be examined (examination point 14)

Y* Position of the examination picture point 13 on the screen y Position of the bed (bed point 15)

y* Position of the mark 11

Y−y=a Position of the examination point 14 with respect to the bed point 15.

Assuming a linear relationship exist between Y and Y* as well as between y and y*, then (I) $Y = c_1 \cdot Y^*$, wherein $c_1$ = positive proportionality constant, (II) $y = c_2 \cdot y^*$, wherein $c_2$ = negative proportionality constant, and (III) $Y - y = a$. Let $c_1$ and $c_2$, for example, be selected such that $c_1 = -c_2$ applies. As a consequence, movement of the mark on the screen of the visual display means always proceeds opposite the movement of the bed.

The following positioning procedure is then executed:

(A) Position bed such that mark 11 resides in the center of the screen, i.e. $y^* = 0 \rightarrow y = 0$ according to (II). Because $Y - y = a$ according to (III). $\rightarrow Y = a$, i.e. examination point 14 is at a.

(B) The stored shot/examination picture point is at $$Y^* \text{ (from } I) = \frac{Y}{c_1} = \frac{a}{c_1}.$$

(C) Position mark to desired examination picture point of the stored image, i.e. the position of the mark is consequently at $$y^* = \frac{a}{c_1}.$$

The positioning of the mark causes a dislocation of the bed into position $$y \text{ (from } II) = c_2 \cdot y^* = c_2 \cdot \frac{a}{c_1}.$$

The examination point 14 is then at $$Y(\text{from III}) = a + y + a = c_2 \cdot \frac{a}{c_1} = a\left(1 + \frac{c_2}{c_1}\right) = 0,$$

i.e. in the center of the ray cone (because $c_1 = -c_2$).

(D) The exposure/examination picture point is then at $$Y^* = \frac{Y}{c_1} = 0,$$

i.e. in the center of the screen.

In the X-ray diagnostics installation described herein, by executing one stored shot the examination point 14 is brought to the center of the X-ray cone without the patient being exposed to an additional radiation dose. The desired examination picture point has been displaced to the center of the screen.

When the desired examination picture point after exposure is not to appear in the center of the screen, but rather at an arbitrary point on the screen, the characteristic mark 11 is positioned to the arbitrary point before producing the stored shot.

The principle described above for positioning the patient bed 4 in the X-ray diagnostics installation disclosed herein can be expanded to control movement of the bed 4 along the other axes by using further variable resistors and video mark generators coupled to the bed along those axes. It is thus possible, for example, by using a second video mark generator for the x-direction, to position the patient with adequate position in the x-y-plane by means of only one stored shot.

Although modifications and changes may be suggested by those skilled in the art it is the intention of the inventor to embody within the patent warranted hereon all changes and modifications as reasonably and properly come within the scope of his contribution to the art.

I claim as may invention:

1. An x-ray diagnostics installation for obtaining an x-ray image of an examination subject comprising:
   a bed on which said patient is disposed movable along at least one axis;
   means for irradiating said patient on said bed with x-radiation;
   an x-ray image intensifier video chain including a display means with a screen for visually displaying said x-ray image;
   a mechanical/electrical transducer means mechanically coupled to said bed for generating an electrical signal corresponding to the position of said bed along said axis; and
   a video mark generator connected to said means for generating an electrical signal and to said display means for generating a video mark on said screen at a location corresponding to the position of said bed along said axis.

2. An x-ray diagnostics installation as claimed in claim 1, wherein said mechanical/electrical transducer means generates an electrical signal which is directly proportional to the position of said bed along said axis.

3. An x-ray diagnostics installation as claimed in claim 1, wherein said mechanical/electrical transducer means for is a variable resistor and a roller disposed adjacent said bed for rotation upon movement of said bed along said axis, rotation of said roller changing the value of said variable resistor as said bed moves along said axis.

* * * * *